United States Patent [19]
King

[11] Patent Number: 6,166,034
[45] Date of Patent: Dec. 26, 2000

[54] SPIRO PIPERIDINE DERIVATIVES AS 5HT1D RECEPTOR ANTAGONISTS

[75] Inventor: Francis David King, Bishops Stortford, United Kingdom

[73] Assignee: SmithKline Beecham p. l. c, Brentford, United Kingdom

[21] Appl. No.: 09/068,432

[22] PCT Filed: Nov. 5, 1996

[86] PCT No.: PCT/EP96/04878

§ 371 Date: May 8, 1998

§ 102(e) Date: May 8, 1998

[87] PCT Pub. No.: WO97/17351

PCT Pub. Date: May 15, 1997

[30] Foreign Application Priority Data

Nov. 8, 1995 [GB] United Kingdom .................... 9522841
Mar. 27, 1996 [GB] United Kingdom .................... 9606398
Mar. 28, 1996 [GB] United Kingdom .................... 9606518

[51] Int. Cl.[7] ...................... A61K 31/445; C07D 401/14; C07D 237/02; C07D 487/20; C07D 493/04

[52] U.S. Cl. ........................... 514/318; 514/326; 546/18; 548/301.7; 549/330; 549/331; 549/343; 549/344

[58] Field of Search ........................... 546/18; 548/301.9; 549/330, 331, 343, 344; 514/318, 326

[56] References Cited

U.S. PATENT DOCUMENTS

| | | | |
|---|---|---|---|
| 5,723,616 | 3/1998 | Houghton et al. | 546/18 |
| 5,919,932 | 7/1999 | Gaster et al. | 546/112 |
| 5,952,325 | 9/1999 | Wyman et al. | 514/212 |
| 5,972,951 | 10/1999 | Gaster et al. | 514/278 |
| 5,972,979 | 10/1999 | Gaster L. | 514/364 |

FOREIGN PATENT DOCUMENTS

| | | |
|---|---|---|
| 0 533 268 A1 | 9/1992 | European Pat. Off. ...... C01D 271/06 |
| 0533268 | 3/1993 | European Pat. Off. . |
| 0 564 358 A1 | 4/1993 | European Pat. Off. .... C07D 491/107 |
| 0564358 | 10/1993 | European Pat. Off. . |
| WO 96/11934 | 4/1996 | WIPO .......................... C07D 491/107 |
| WO 96/19477 | 6/1996 | WIPO .......................... C07D 471/10 |
| 97/10824 | 3/1997 | WIPO . |

OTHER PUBLICATIONS

Clitherow, et al., J. Med. Chem; vol. 37, No. 15, 1994, pp. 2253–2257.

*Primary Examiner*—Alan L. Rotman
*Assistant Examiner*—Rita Desai
*Attorney, Agent, or Firm*—James M. Kanagy; Charles M. Kinzig

[57] ABSTRACT

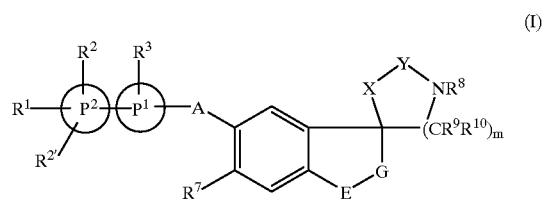

Novel spiro piperdine derivatives of formula (I), in which $P^1$, $P^2$, $R^1$, $R^2$, $R^{2'}$, $R^3$, m, A, E, G, X, Y, $R^7$, $R^8$, $R^9$ and $R^{10}$ have the meanings defined in claim 1 are described, as well as their use for preparing medicaments which have 5HT1D receptor antagonist activity.

8 Claims, No Drawings

SPIRO PIPERIDINE DERIVATIVES AS 5HT1D RECEPTOR ANTAGONISTS

This is a 371 of International Application PCT/EP96/04878, filed Nov. 5, 1996.

The present invention relates to novel piperidine derivatives, processes for their preparation and pharmaceutical compositions containing them.

EPA 0 533 266/7/8 disclose a series of benzanilide derivatives which are said to possess $5HT_{1D}$ receptor antagonlist activity. PCT/EP/95/04889 discloses further $5HT_{1D}$ receptor antagonist having a spiropiperidine structure. These compounds are said to be of use in treatment of various CNS disorders. The $5HT_{1D\beta}$ receptor has now been reclassified as the $5HT_{1B}$ receptor (P. R. Hartig et al Trends in Pharmacological Science, 1996, 17, 103–105.

A structurally distinct class of compounds have now been discovered and have been found to exhibit $5HT_{1D}$ antagonist activity. In a first aspect, the present invention therefore provides a compound of formula (I) or a salt or N-oxide thereof:

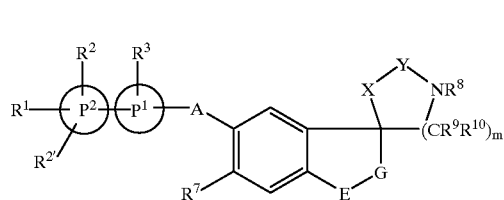

(I)

in which

P¹ and P² are independently phenyl, napthyl, a 5 to 7-membered heterocyclic ring selected from the group consisting of thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl, or a bicyclic heterocyclic ring selected from the group consisting of include quinoline, isoquinoline, benzofuran and benzothiophene;

R¹ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $N=CNR^9NR^{10}R^{11}$, $NR^{10}CO_2R^{11}$, $NR^{10}CO(CH_2)_pNR^{10}R^{11}$, $NR^{10}CONR^{10}R^{11}$, $CR^{10}=NOR^{11}$, $CNR^{10}=NOR^{11}$, or $NR^{12}COR^{13}$ where $R^9$, $R^{10}$ and $R^{11}$ are independently hydrogen or $C_{1-6}$alkyl, p is 1 to 4, $R^{12}$ is hydrogen, $C_{1-6}$alkyl or together with $R^{2'}$ forms a group $(CH_2)_q$ where q is 2, 3 or 4 and $R^{13}$ is hydrogen, $C_{1-6}$alkyl or an aryl group; or R¹ is a 5 to 7-membered heterocyclic ring selected from the group consisting of thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl optionally substituted by $C_{1-6}$alkyl;

R² and R³ are independently hydrogen, halogen, $C_{1-6}$alkyl; $C_{3-6}$cycloalkenyl, $C_{1-6}$alkoxy, hydroxy$C_{1-6}$alkyl, $C_{1-6}$alkylOC$_{1-6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1-6}$alkyl, or $R^2$ and $R^3$ together form a group $-(CH_2)_r-R^{14}-(CH_2)_s-$ where $R^{14}$ is O, S, $CH_2$ or $NR^{15}$ where $R^{15}$ is hydrogen or $C_{1-6}$alkyl and r and s are independently 0, 1 or 2;

A is a group

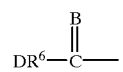

(i)

or a group

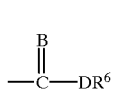

(ii)

where

B is oxygen or sulphur and D is nitrogen, carbon or a CH group; and $R^6$ is hydrogen or $C_{1-6}$alkyl and $R^7$ is $C_{1-6}$alkyl, $C_{1-6}$alkoxy or halogen, or $R^6$ together with $R^7$ forms a group —M— where M is $(CR^{16}R^{17})_t$ where t is 1, 2 or 3 and $R^{16}$ and $R^{17}$ are independently hydrogen or $C_{1-6}$alkyl or M is $(CR^{16}R^{17})_u$-J where u is 0, 1 or 2 and J is oxygen, sulphur, $CR^{16}=CR^{17}$, $CR^{16}=N$, or $N=N$;

$R^8$ is hydrogen or $C_{1-6}$alkyl;

$R^9$ and $R^{10}$ are independently hydrogen or $C_{1-6}$alkyl;

E is oxygen, $CR^{18}R^{19}$ or $NR^{20}$ where $R^{18}$, $R^{19}$ and $R^{20}$ are independently hydrogen or $C_{1-6}$alkyl or E is $S(O)_v$ where v is 0, 1 or 2;

G is C= or $CR^{21}R^{22}$ where $R^{21}$ and $R^{22}$ are independently hydrogen or $C_{1-6}$alkyl;

X and Y are independently $CR^9R^{10}$ where $R^9$ and $R^{10}$ are as defined above; and m is 1, 2 or 3, provided that P¹ and P² are not both phenyl.

$C_{1-6}$alkyl groups, whether alone or as part of another group, may be straight chain or branched.

When P¹ and P² are bicyclic heterocyclic rings suitable examples include quinoline, isoquinoline, benzofuran and benzothiophene. When P¹ and P² are monocyclic heterocyclic rings suitable examples include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl Preferably P¹ is phenyl. Preferably P² is a bicyclic aryl ring, in particular naphthyl. The P¹ and P² groups can be attached to the remainder of the molecule at any suitable points.

Preferably R¹ is $NR^{12}COR^{13}$ or a 5–7 membered heterocyclic ring. When R¹ is a 5 to 7-membered heterocyclic ring suitable examples include aromatic groups such as thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. Saturated and partially saturated rings are also within the scope of the invention, in particular rings including an oxo or thioxo moiety such as lactams and thiolactams. The heterocyclic rings can be linked to the remainder of the molecule via a carbon atom or, when present, a nitrogen atom. Suitable substituents for these rings include R² and R³ groups as defined above. Preferably R¹ is optionally substituted oxadiazolyl or an optionally substituted lactam ring. Preferred substituents for oxadiazolyl groups include $C_{1-6}$alkyl such as methyl. Most preferably R¹ is a 5-methyl-1,3,4-oxadiazol-3-yl group or a 2-oxo-pyrrolidin-1-yl group.

Preferably $R^2$ and $R^3$ are both hydrogen.
Preferably A is a group of formula (i).
Preferably B is oxygen.
Preferably D is nitrogen.

$R^6$ together with $R^7$ forms a group —M— where M is $(CR^{16}R^{17})_t$ where t is 2 or 3 and $R^{16}$ and $R^{17}$ are both hydrogen.

Preferably $R^8$ is hydrogen or methyl. Preferably m is 2 forming a spiro-piperidine ring, Preferably $R^9$ and $R^{10}$ are both hydrogen.

Suitably E is oxygen, $CR^{18}R^{19}$ or $NR^{20}$ where $R^{18}$, $R^{19}$ and $R^{20}$ are independently hydrogen or $C_{1-6}$alkyl or E is $S(O)_v$ where v is 0, 1 or 2. Preferably E is oxygen.

Suitably G is C=O or $CR^{21}R^{22}$ where $R^{21}$ and $R^{22}$ are independently hydrogen or $C_{1-6}$alkyl. Preferably G is $CH_2$.

Suitably X and Y are independently $CR^9R^{10}$ where $R^9$ and $R^{10}$ are as defined above. Preferably X and Y are both $CH_2$.

Particularly preferred compounds of the invention include:

5-[4-{5-(5-Methyl-1,3,4-oxadiazol-2-yl)-1-naphthyl}benzoyl]-1'-methyl-2,3,6,7-tetrahydrospiro[furo[2,3-f]indole-3,4'-piperidine], 5-[4-{5-(5-Methyl-1,3,4-oxadiazol-2-yl)-1-naphthyl}benzoyl]-2,3,5,6,7,8-methylspiro[furo[2,3-g]quinoline-3,4'-piperidine], 5-[4-{5-(5-Methyl-1,3,4-oxadiazol-2-yl)-1-naphthyl}-3-methylbenzoyl]-1'-methyl-2,3,6,7-tetrahydrospiro[furo[2,3-f]indole-3,4'-piperidine], 5-[4-{5-(5-Methyl-1,3,4-oxadiazol-2-yl)-1-naphthyl}-3-methylbenzoyl]-2,3,5,6,7,8-hexahydro-1'-methylspiro[furo[2,3-g]quinoline-3,4'-piperidine], 1'-Methyl-5-[4-(2-methyl-6-(2-oxopyrrolidin-1-yl)pyridin-3-yl)benzoyl]-2,3,6,7- tetrahydrospiro[furo[2,3-f]indole-3,4'-piperidine], 5-[4-(2-Methyl-6-(2-oxopyrrolidin-1-yl)pyridin-3-yl)benzoyl]-2,3,6,7-tetrahydrospiro[furo[2,3-f]indole-3,4'-piperidine], 1'-Methyl-5-[6-(2-methyl-4-(5-methyl-1,3,4-oxadiazol-2-yl)phenyl)nicotinoyl]-2,3,6,7-tetrahydrospiro[furo[2,3-f]indole-3,4'-piperidine], or pharmaceutically acceptable salts and N-oxides thereof.

Preferred salts of the compounds of formula (I) are pharmaceutically acceptable salts. These include acid addition salts such as hydrochlorides, hydrobromides, phosphates. acetates, fumarates, maleates. tartrates. citrates. oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises:

(a) for compounds of formula (I) where D is nitrogen and B is oxygen, reaction of a compound of formula (II):

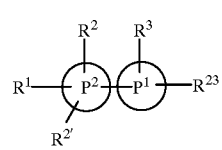

(II)

in which $P^1$, $P^2$, $R^1$, $R^2$, $R^{2'}$ and $R^3$ are as defined in formula (I);

with a compound of formula (III):

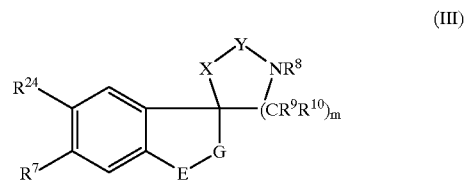

(III)

wherein $R^6$, $R^7$, $R^8$, $R^9$, $R^{10}$, E, G, X, Y, and m are as defined in formula (I and $R^{23}$ and
$R^{24}$ are functional groups which react together to form the A group; and optionally thereafter in any order:
converting a compound of formula (I) into another compound of formula (I) forming a pharmaceutically acceptable salt.

Suitably one of $R^{23}$ or $R^{24}$ is —COL where L is a leaving group and the other is $NHR^6$ where $R^6$ is as defined above.

Suitable activated carboxylic acid derivatives of formula (II)/(III) include acyl halides and acid anhydrides. For example L can be chloro such that one of $R^{23}$ or $R^{24}$ is an acid chloride group COCl which can be reacted with a compound where $R^{23}$ or $R^{24}$ is $NHR^6$. Activated compounds can also be prepared by reaction of the corresponding carboxylic acid with a coupling reagent such as carbonyldiimidazole, dicyclohexylcarbodiimide or diphenylphosphorylazide Preferably the group L is halo, particularly chloro.

Compounds of formulae (II) and (III) are typically reacted together in an inert organic solvent such as DMF, THF or dichloromethane at ambient or elevated temperature in the presence of a base such as an alkali metal hydroxide, triethylamine or pyridine.

Alternatively L is an ester forming group such that the resulting esters of formula (II) can be reacted with compounds of formula (III) in the presence of an organoaluminium reagent such as trimethylaluminium. Such a reaction is typically carried out in the presence of an inert solvent such as toluene.

Intermediate compounds of formula (II) and (III) can be prepared using standard procedures known in the art. Certain intermediate compounds of formula (II) and (III) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals. thioacetals or thioketals. Deprotection is achieved using standard conditions.

Compounds of formula (I) can be converted into further compounds of formula (I) using standard procedures known in the art. For example amino groups can be alkylated using base and an alkyl halide.

$5HT_{1B}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and ageassociated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1B}$ Antagonists. and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs. or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved. and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

Methyl 5-bromo-1-napthoate

5-Bromonapthoic acid (*J Chem. Soc.*, 1950, 991) (5.13 g, 20 mmol) was added to a solution of thionyl chloride (10 ml) in methanol (200 ml). The mixture was stirred at reflux for 4 h, yielding a dark brown solution. On cooling, the title compound precipitated as a light brown solid, which was filtered off and dried, yielding 5.34 g material (98%).

$^1$H NMR (200 MHz, CDCl$_3$) δ(ppm): 8.89 (d, 1H), 8.51 (d, 1H), 8.21 (d, 1H), 7.85(d, 1H), 7.61 (dd, 1H), 7.44 (dd, 1H), 4.01 (s, 3H)

DESCRIPTION 2

5-Bromo-1-napthoic hydrazide

Methyl 5-bromo-1-naphthoate (D1) (5.32 g, 20 mmol) and hydrazine hydrate (5.7 ml, 100 mmol) were stirred at reflux in methanol (50 ml) for 48 h. After cooling, the solid was filtered off, washed with cold methanol, and dried in vacuo at 60° C., yielding the title compound (3.48 g, 65%) as a grey-brown crystalline powder.

$^1$H NMR (250 MHz, d$^6$DMSO) δ(ppm): 9.77 (s, 1H), 8.24 (t, 2H), 7.95 (d, 1H), 7.72 (t, 1H), 7.64 (d, 1H), 7.50 (t, 1H), 4.62 (s, 2H).

DESCRIPTION 3

2-(5-Bromo-1-naphthyl)-5-methyl-1,3,4-oxadiazole

5-Bromo-1-napthoic hydrazide (D2) (2.00 g, 7.5 mmol) was stirred at reflux under Ar in triethyl orthoacetate (20 ml) for 20 h. The mixture was cooled in ice, and the solid was filtered off, washed with petroleum ether (b.p. 60–80° C.), and dried in vacuo at 60° C., giving the title compound (1.92 g, 88%) as a light brown powder.

$^1$H NMR (200 MHz, CDCl$_3$) δ(ppm): 9.26 (d, 1H), 8.49 (d, 1H), 8.18 (d, 1H), 7.90 (d, 1H), 7.67 (t, 1H), 7.50 (t, 1H), 2.69 (s, 3H).

DESCRIPTION 4

1-(4-Carboxyphenyl)-5-(5-methyl-1,3,4-oxadiazol-2-yl)naphthalene 2-(5-Bromo-1-naphthyl)-5-methyl-1,3,4-oxadiazole (D3) (1.50 g, 5.2 mmol) and 4-carboxyphenylboronic acid (0.86 g, 5.2 mmol) were stirred in dimethoxyethane (DME) (40 ml), and sodium carbonate (2.5 g, 23 mmol) in water (40 ml) was added. The mixture was purged by a stream of Ar for 15 min, when tetrakis (triphenylphosphine)palladium (0) (0.1 g, 0.008 mmol) was added. The mixture was stirred at reflux under Ar for 20 h, and then evaporated to remove DME. The grey suspension was acidified (5M HCl), and the solid was filtered off and dried in vacuo at 60° C. This material was heated at reflux in ethanol (30 ml), and filtered hot. The white solid so collected was dried in vacuo at 60° C. giving 1.32 (77%) of the title compound.

$^1$H NMR (250 MHz, d$^6$DMSO) δ(ppm): 9.15 (d, 1H), 8.19 (d, 1H), 8.12 (d, 2H), 8.00 (d, 1H), 7.81 (t, 1H), 7.66 (t, 1H), 7.6 (m, 3H), 2.67 (s, 3H).

DESCRIPTION 5

3-Methyl-4-[5-(5-methyl-1,3,4-oxadiazol-2-yl) naphth-1-yl]benzoic acid

The title compound was prepared from 2-(5-bromo-1-naphthyl)-5-methyl-1,3,4-oxadiazole (D3, 395 mg; 1.36 mmol) and 4-borono-3-methylbenzoic acid (D3 in WO 96/19477,246 mg; 1.36 mmol) following a similar method to description 4, as a cream solid (305 mg, 65%).

$^1$H NMR (200 MHz, d$^6$DMSO) δ(ppm): 13.02 (s. 1H), 9.12 (d, 1H), 8.17 (d, 1H), 8.0 (s, 1H), 7.9 (d, 1H), 7.8 (t, 1H), 7.69–7.42 (m, 3H), 7.35 (d, 1H), 2.65 (s, 3H), 2.0 (s, 3H).

DESCRIPTION 6

4-(6-Amino-2-methylpyridin-3-yl)benzoic acid hydrochloride

The title compound was prepared from 6-amino-3-bromo-2-methylpyridine using a similar procedure to Description 4, as a grey solid (78%).

$^1$H NMR (250 MHz, d$^6$DMSO) δ(ppm): 8.12 (br s, 2H), 8.02 (d, 2H), 7.88 (d, 1H), 7.54 (d, 2H), 6.97 (d, 1H), 2.43 (s, 3H).

DESCRIPTION 7

Methyl 4-(6-amino-2-methylpyridin-3-yl)benzoate

A stirred suspension of 4-(6-amino-2-methylpyridin-3-yl)benzoic acid hydrochloride (D6, 1.9 g, 8.3 mmole) in methanol (120 ml) was treated with conc. HCl acid (1 ml) and heated under reflux for 2 h. The solution was concentrated in vacuo, the residue treated with excess 10% Na$_2$CO$_3$ solution and extracted with ethyl acetate. The extract was dried (Na$_2$SO$_4$) and concentrated in vacuo to afford the title compound as a pale yellow solid (1.4 g, 70%).

$^1$H NMR (200 MHz, d$^6$DMSO) δ(ppm): 7.98 (d, 2H), 7.45 (d, 2H), 7.30 (d, 1H), 6.35 (d, 1H), 6.05 (br s, 2H), 3.87 (s, 3H), 2.25 (s, 3H).

DESCRIPTION 8

Methyl 4[6-(4-chlorobutanoylamino)-2-methylpyridin-3-yl]benzoate

A stirred suspension of methyl 4-(6-amino-2-methylpyridin-3-yl)benzoate (D7, 1.0 g, 4.1 mmole) in dichloromethane (80 ml) was treated with pyridine (0.66 ml, 8.2 mmole), followed by 4-chlorobutyryl chloride (0.47 ml, 4.3 mmole). The resulting solution was stirred at 25° C. for 2 h, then treated with 5% Na$_2$CO$_3$ solution and after 30 minutes, the organic layer was separated, dried (Na$_2$SO$_4$) and concentrated in vacuo to leave a pale yellow solid. This was recrystallised from ethyl acetate/60–80 petrol to afford the title compound as a beige solid (1.13 g, 80%).

DESCRIPTION 9

Methyl 4[2-methyl-6-(2-oxopyrrolidin-1-yl)pyridin-3-yl]benzoate

A stirred solution of methyl 4[6-(4-chlorobutanoylamino)-2-methylpyridin-3-yl]benzoate (D8, 0.60 g, 1.7 mmole) in DMF (7 ml) at 25° C. under argon was treated portionwise over 15 minutes with potassium t-butoxide (0.23 g, 2.0 mmole). The mixture was stirred for 3 h, then poured into water (100 ml) and extracted with ethyl acetate. The extract was washed with water, dried (Na$_2$SO$_4$) and concentrated in vacuo to afford the title compound as an orange solid (0.45 g, 85%).

$^1$H NMR (250 MHz, CDCl$_3$) δ(ppm): 8.26 (d, 1H), 8.10 (d, 2H), 7.55 (d, 1H), 7.40 (d, 2H), 4.16 (t, 2H), 3.96 (s, 3H), 2.69 (t, 2H), 2.44 (s, 3H), 2.15 (quintet, 2H).

DESCRIPTION 10

Methyl 6-(trifluoromethylsulphonyloxy)nicotinate

Methyl 6-hydroxynicotinate (J. Am. Chem. Soc., 1982, 1428–30) (9.00 g, 0.058 mol) was dissolved in dry pyridine (150 ml) and was treated with trifluoromethanesulphonic anhydride (10.73 ml, 0.064 mol), dropwise with stirring under argon with ice cooling. After 2 h, a further amount of trifluoromethanesulphonic anhydride (2.68 ml, 0.016 mol) was added, and the mixture was stirred for a further 1 h before being left standing at room temp. overnight. The reaction mixture was then evaporated under reduced pressure, and the residue partitioned between dichloromethane and sodium hydrogen carbonate solution. The organic layer was then washed with sodium hydrogen carbonate solution, dried (Na$_2$SO$_4$) and evaporated under reduced pressure to give a brown oil, which was azeotroped with toluene (2×) and dried in vacuo to give the title compound as a brown oil (1 1.07 g, 67%).

$^1$H NMR (250 MHz, CDCl$_3$) δ(ppm): 9.00 (d, 1H), 8.51 (dd, 1H), 7.25 (d, 1H), 3.98 (s, 3H).

DESCRIPTION 11

Methyl 6-(trimethylstannyl)nicotinate

Methyl 6-(trifluoromethylsulphonyloxy)nicotinate (D10, 3.89 g, 0.0136 mol) was dissolved in dry dioxane (100 ml) and was treated with lithium chloride (1.73 g, 0.041 mol), followed by 2,6-di-$^t$butyl-4-methylphenol (0.030 g), and hexamethyldistannane (5.00 g, 0.015 mol). The mixture was flushed with argon and tetrakis(triphenylphosphine) palladium(0) (0.786 g, 0.007 mol) was added. The resulting mixture was then heated to reflux with stirring under argon.

After 4 h, the reaction mixture was allowed to cool and was left at room temperature overnight. The reaction mixture was then filtered through kieselguhr and the filter pad was washed with dichloromethane (70 ml). The filtrate was then evaporated under reduced pressure and the residue was partitioned between diethyl ether and water. The organic layer was then washed with 15% ammonia solution (2×), dried ($Na_2SO_4$) and evaporated under reduced pressure to give the title compound as a brown oil, which was dried in vacuo (2.886 g, 71%).

$^1$H NMR (200 MHz, $CDCl_3$) δ(ppm): 9.30 (d, 1H), 8.08 (dd, 1H), 7.54 (d, 1H), 3.91 (s, 3H), 1.38 (s, 9H).

DESCRIPTION 12

Methyl 6-[2-methyl-4-(5-methyl-1,3,4-oxadiazol-2-yl)phenyl]nicotinate

Methyl 6-(trimethylstannyl)nicotinate (D11, 0.300 g, 1.00 mmol) was dissolved in dry toluene (15 ml) and was treated with 2-(4-bromo-3-methylphenyl)-5-methyl-1,3,4-oxadiazole (EP 0533268A1) (0.211 g, 0.834 mmol). The mixture was flushed with argon and bis(triphenyl phosphine) pallalladium (II) chloride (0.029 g, 0.042 mmol) was added. The mixture was then heated to reflux under argon. After 2 h, further methyl 6-(trimethylstannyl)nicotinate (0.030 g, 0.100 mmol) in toluene (2 ml) and bis(triphenylphosphine) palladium (II) chloride (0.010 g, 0.014 mmol) was added. Reflux was continued for a further 2 h before the reaction mixture was allowed to cool. The reaction mixture was then filtered through kieselguhr. The kieselguhr was washed with toluene (2×20 ml) and the filtrate was evaporated under reduced pressure to give a yellow/brown solid which was dried in vacuo (0.450 g). The solid was then purified by silica-gel chromatography (1:1 Petrol 60–80: EtOAc as eluant) to give the title compound as a cream coloured solid (0.140 g, 54%).

$^1$H NMR (250 MHz, $CDCl_3$) δ(ppm): 9.32 (d, 1H), 8.38 (dd, 1H), 8.03 (s, 1H), 7.95 (d, 1H), 7.55 (m, 2H), 3.97 (s, 3H), 2.57 (s, 3H), 2.49 (s, 3H).

EXAMPLE 1

5-[4-{5-(5-Methyl-1,3,4-oxadiazol-2-yl)-1-naphthyl}benzoyl]-1'-methyl-2,3,6,7-tetrahydrospiro [furo[2,3-f]indole-3,4'-piperidine]hydrochloride 1-(4-Carboxyphenyl)-5-(5-methyl-1,3,4-oxadiazol-2-yl) naphthalene (D4) (0.49 g, 0.45 mmol) in dichloromethane was treated with oxalyl chloride (0.047 ml, 0.53 mmol) followed by 1 drop of DMF. This mixture was stirred under Ar for 1 h, washed with potassium carbonate/brine solution, dried ($Na_2SO_4$) and evaporated to give a white solid. This was redissolved in dichloromethane (10 ml), and treated with 1'-methyl-2,3,6,7-tetrahydrospiro[furo[2,3-f]indole-3, 4'-piperidine (D8 in WO 96/19477, 0.100 g, 0.41 mmol) and triethylamine (0.09 ml, 0.65 mmol). The mixture was stirred for 1 h, washed with potassium carbonate/brine solution, dried ($Na_2SO_4$) and evaporated. The crude material was purified by chromatography on silica gel, eluting with 0–10% methanol/dichloromethane. This gave the free base of the title compound (0.154 g, 67%) as white solid. This was dissolved in dichloromethane, treated with 1M HCl in ether
(0.55 ml), and then diluted with ether (20 ml). This gave, after filtration and drying, the title compound (0.125 g) as a white solid.

$^1$H NMR(200 MHz, d$^6$DMSO) δ(ppm): 10.32 (b, 1H), 9.16 (d, 1H), 8.23 (d, 1H), 8.09 (d, 1H), 7.98 (b, 1H), 7.7–7.9 (m, 4H), 7.55–7.7 (m, 3H), 6.80 (s, 1H), 4.53 (s, 2H), 4.12 (t, 2H), 3.45 (m, 2H), 3.0–3.2 (m, 4H), 2.80 (bs, 3H), 2.68 (s, 3H), 2.2 (m, 2H), 1.91 (m, 2H).

EXAMPLE 2

5-[-{5-(5-Methyl-1,3,4-oxadiazol-2-yl)-1-naphthyl}benzoyl]-2,3,5,6,7,8-hexahydro-1'-methylspiro [furo[2,3-g]quinoline-3,4'-piperidine1] hydrochloride Similar procedure to Example 1, using D4 and 2,3,5,6,7, 8-hexahydro-1'-methylspiro [furo[2,3-g]quinoline-3,4'-piperidine](D10 in WO 96/19477).

$^1$H NMR (200 MHz, d$^6$DMSO) δ(ppm): 10.6 (bs, 1H), 9.12 (d, 1H), 8.22 (d, 1H), 8.11 (d, 1H), 7.8 (m, 2H), 7.59 (d, 1H), 7.44 (m, 4H), 6.69 (s, 1H), 6.47 (b, 1H), 4.40 (s, 2H), 3.83 (m, 2H), 3.2 (m, 2H), 2.95 (m, 2H), 2.7 (m, 5H), 2.67 (s, 3H), 1.75–2.1 (m, 4H), 1.55–1.7 (m, 2H).

EXAMPLE 3

5-[4-{5-(5-Methyl-1,3,4-oxadiazol-2-yl)-1-naphthyl}-3-methylbenzoyl]-1'-methyl-2,3,6,7-tetrahydrospiro[furo[2,3-f]indole-3,4'-piperidine] hydrochloride The title compound was prepared from 3-methyl-4-[5-(5-methyl-1,3,4-oxadiazol-2-yl) naphth-1-yl]benzoic acid (D5, 150 mg; 0.436 mmol) and 1'-methyl-2,3,6,7-tetrahydrospiro [furo[2,3-f]indole-3,4'-piperldine] (D8 in WO 96/19477, 106 mg; 0.43 mmol) following the procedure outlined in Example 1, as a white powder (96 mg, 36%).

$^1$H NMR (free base) (200 MHz, $CDCl_3$) δ(ppm): 9.28 (d, 1H), 8.15 (d, 2H), 7.8–7.61 m, 2H), 7.6–7.4 (m, 4H), 7.3 (d, 1H), 6.7 (s, 1H), 4.4 (s, 2H), 4.29–4.1 (m, 2H), 3.1 (t, 2H), 2.95 (brs, 2H), 2.71 (s, 3H), 2.41 (s, 3H), 2.3–2.0 (m, 7H), 1.96–1.72 (m, 2H).

EXAMPLE 4

5-[4-{5-(5-Methyl-1,3,4-oxadiazol-2-yl)-1-naphthyl}-3-methylbenzoyl]-2,3,5,6,7,8-hexahydro-1'-methylspiro [furo[2,3-g]quinoline-3,4'-piperidine] hydrochloride The title compound was prepared from 3-methyl-4-[5-(5-methyl-1,3,4-oxadiazol-2-yl)naphth-1-yl]benzoic acid (D5, 125 mg; 0.363 mmol) and 2,3,5,6,7,8-hexahydro-1'-methylspiro[furo[2,3-g]quinoline-3,4'-piperidine] (D10 in WO 96/19477, 94 mg; 0.363 mol) following the procedure outlined in Example 1, as a white powder (88 mg, 39%).

$^1$H NMR (free base) (200 MHz, $CDCl_3$) δ(ppm): 9.24 (d, 1H), 8.12 (d, 1H), 7.73–7.55 (m, 2H), 7.46–7.25 (m, 3H), 7.1 (s, 2H), 6.6 (s, 1H), 6.5 (br s, 1H), 4.28 (s, 2H), 3.95 (t, 2H), 2.85–2.58 (m, 7H), 2.3 (s, 3H), 2.13–1.85 (m, 7H), 1.8–1.45 (m, 4H).

EXAMPLE 5

1'-Methyl-5-[4-(2-methyl-6-(2-oxopyrrolidin-1-yl) pyridin-3-yl)benzoyl]-2,3,6,7-tetrahydrospiro[furo[2, 3-f]indole-3,4'-piperidine1]

A stirred solution of 1'-methyl-2,3,6,7-tetrahydrospiro [furo[2,3-f]-indole-3,4'-piperidine] (D8 in WO 96/19477, 250 mg, 1.0 mmole) in toluene (15 ml) at 25° C. under argon was treated with trimethylaluminium (0.56 ml of 2M solution in toluene, 1.1 mmole). After 15 minutes a solution of methyl 4-[2'-methyl-6-(2-oxopyrrolidin-1-yl)pyridin-3-yl]benzoate (D9, 320 mg, 1.0 mmole) in toluene (7 ml) was added and the mixture heated under reflux for 2 h. The reaction mixture was allowed to cool, then poured into a stirred slurry of silica gel (20 g) in dichloromethane (30 ml), stirred for 15 minutes, then loaded into a chromatography column and eluted with 0–10% methanol/dichloromethane. The title compound was obtained as a yellow foam (163 mg, 31%), which was converted to its hydrochloride salt and crystallised from acetone/ether as a white solid.

$^1$H NMR (free base) (250 MHz, CDCl$_3$) δ(ppm): 8.26 (d, 1H), 8.13 (br s, 1H), 7.60 (d, 2H), 7.55 (d, 1H), 7.40 (d, 2H), 6.67 (s, 1H), 4.40 (br s, 2H), 4.22–4.00 (m, 2H), 4.15 (t, 2H), 3.06 (t, 2H), 3.00–2.75 (br m, 2H), 2.69 (t, 2H), 2.45 (s, 3H), 2.32 (br s, 3H), 2.25–160 (m, 6H), 2.13 (quintet, 2H).

EXAMPLE 6

5-[4-(2-Methyl-6-(2-oxopyrrolidin-1-yl)pyridin-3-yl)benzoyl]-2,3,6,7-tetrahydrospiro[furo[2,3-f]indole-3,4'-piperidine]

1'-Methyl-5-[4-(2-methyl-6-(2-oxopyrrolidin-1-yl)pyridin-3-yl]benzoyl]-2,3,6,7-tetrahydrospiro[furo[2,3-f]indole-3,4'-piperidine] (E5, 0.30 g, 0.59 mmol) was stirred under argon in 1,2-dichloroethane (20 ml) with dilsopropylethylamine (0.15 ml, 0.89 mmol) and 1-chloroethyl chloroformate (0.16 ml, 1.5 mmol) for 16 h. The mixture was concentrated in vacuo, and the residue was heated at reflux in methanol (100 ml) for 1.5 h. The solution was evaporated to dryness, and this residue was dissolved in dichloromethane, washed with 10% Na$_2$CO$_3$, dried (Na$_2$SO$_4$) and evaporated to dryness. The material was purified by conversion to the N-t-butoxycarbonyl derivative (di-t-butyldicarbonate, CH$_2$Cl$_2$, 1h), chromatography, and deprotection with trifluoroacetic acid to afford the title compound. The hydrochloride salt was formed by dissolution in dichloromethane, treatment with 1 M HCl in Et$_2$O, and trituration in acetone. This gave 0. 123 g, 39% of a white powder.

$^1$H NMR (HCl salt) (250 MHz, d$^6$DMSO) δ(ppm): 9.25 (d, 1H), 8.77 (d, 1H), 8.22 (d, 1H) 7.97 (s, 1H), 7.72 (d, 1H), 7.68 (d, 2H), 7.51 (d, 2H), 6.77 (s, 1H), 4.52 (s, 2H), 4.05 (t, 4H), 3.31 (bd, 2H), 3.04 (t, 2H), 3.0 (m, 2H), 2.60 (t, 2H), 2.45 (s, 3H), 2.1 (m, 4H), 1.83 (bd, 2H).

EXAMPLE 7

1'-Methyl-5-[6-(2-methyl-4-(5-methyl-1,3,4-oxadiazol-2-yl)phenyl) nicotinoy]-2,3,6,7tetrahydrospiro[furo[2,3-f]indole-3,4'-piperidinel]

1'-Methyl-2,3,6,7-tetrahydrospiro[furo[2,3-f]indole-3.4'-piperidine] (D8 in WO 96/19477, 0.092 g, 0.379 mmol) was dissolved in toluene (5 ml) and was treated with trimethylaluminum (2.0 M in hexanes) (0.760 ml, 1.516 mmol) with stirring under argon. After 15 minutes a suspension of methyl 6-[2-methyl-4-(5-methyl-1,3,4-oxadiazol-2-yl)phenyl]nicotinate (D12, 0.130 g, 0.421 mmol) in toluene (14 ml) was added. The reaction mixture was then heated to 80° C. with stirring. After 4 h, the reaction mixture was allowed to cool and was left at room temperature overnight. A further amount of trimethylaluminium (2.0M in hexanes) (0.760 ml, 1.516 mmol) was then added. The reaction mixture was then heated to reflux with stirring. After 4 h, the reaction mixture was allowed to cool and was poured into a slurry of silica-gel (9385~10 g) in dichloromethane (50 ml). After effervescence had ceased, the reaction mixture was filtered and the filter pad washed with 20% MeOH/CH$_2$Cl$_2$ (250 ml). The filtrate was then evaporated under reduced pressure to give a yellow solid which was purified by silica-gel chromatography (7.5% MeOH/CH$_2$Cl$_2$ as eluant) to give the title compound as a yellow solid (0.020 g, 10%), which was converted to its oxalate salt, m.pt. 206–210° C.

$^1$NMR (250 MHz, CDCl$_3$) (free base) δ(ppm): 8.91 (s, 1h), 8.91 (s, 1h), 7.98 (m; 3h), 7.58 (m, 2h), 6.70 (s, 1h), 4.40 (s, 2h), 4.15 (m, 2h), 3.12 (t, 2h), 2.92 (m2H), 2.6 (s, 3h), 2.48 (s, 3H), 2.40 (s, 3H), 2.15 (m, 4h), 1.85 (m, 2h)

What is claimed is:

1. A compound of formula (I) or a pharmaceutically acceptable salt or N-oxide thereof:

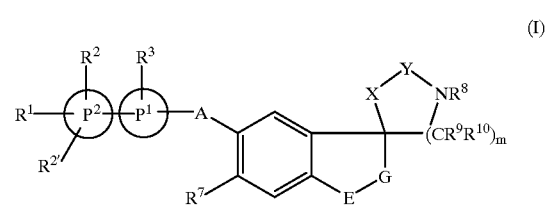

(I)

in which

P$^1$ and P$^2$ are independently phenyl, napthyl, or pyridyl;

R$^1$ is oxadiazolyl, or 2-oxopyrrolidin-1-yl, unsubstituted or substituted by C$_{1-6}$alkyl;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl,OC$_{1-6}$alky, aryl acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl, or R$^2$ and R$^3$ together form a group —(CH$_2$)$_r$—R$^{14}$—(CH$_2$)$_s$— where R$^{14}$ is O, S, CH$_2$ or NR$^{15}$ where R$^{15}$ is hydrogen or C$_{1-6}$alkyl and r and s are independently 0, 1 or 2;

A is a group

(i)

or a group

(ii)

where

B is oxygen or sulphur and D is nitrogen, or a CH group; and

R$^6$ together with R$^7$ forms a group —M— where M is (CR$^{16}$R$^{17}$)$_t$ where t is 2 or 3 and R$^{16}$ and R$^{17}$ are independently hydrogen or C$_{1-6}$alkyl;

R$^8$ is hydrogen or C$_{1-6}$alkyl;

R$^9$ and R$^{10}$ are independently hydrogen or C$_{1-6}$alkyl;

E is oxygen, CR$^{18}$R$^{19}$ or NR$^{20}$ where R$^{18}$, R$^{19}$ and R$^{20}$ are independently hydrogen or C$_{1-6}$alkyl or E is S(O)$_v$ where v is 0, 1 or 2;

G is C═O or CR$^{21}$R$^{22}$ where R$^{21}$ and R$^{22}$ are independently hydrogen or C$_{1-6}$alkyl;

X and Y are independently $CR^9R^{10}$ where $R^9$ and $R^{10}$ are as defined above; and m is 2;

provided that $P^1$ and $P^2$ are not both phenyl.

2. A compound according to claim 1 in which $P^2$ is naphthyl.

3. A compound according to claim 1 in which $R^2$ is $C_{1-6}$alkyl.

4. A compound claim 1 in which $R^4$ is $C_{1-6}$ alkyl.

5. A compound claim 1 in which n is 1 and $R^5$ and $R^6$ are hydrogen.

6. A compound according to claim 1 which is:

5-[4-{5-(5-Methyl-1,3,4-oxadiazol-2-yl)-1-naphthyl}benzoyl]-1'-methyl-2,3,6,7-tetrahydrospiro[furo[2,3-f]indole-3,4'-piperidine], 5-[4-{5-(5-Methyl-1,3,4-oxadiazol-2-yl)-1-naphthyl}benzoyl]-2,3,5,6,7,8-hexahydro-1'-methylspiro[furo[2,3-g]quinoline-3,4'-piperidine], 5-[4-{5-(5-Methyl-1,3,4-oxadiazol-2-yl)-1-naphthyl}-3-methylbenzoyl]-1'-methyl-2,3,6,7-tetrahydrospiro[furo[2,3-f]indole-3,4'-piperidine], 5-[4-{5-(5-Methyl-1,3,4-oxadiazol-2-yl)-1-naphthyl }-3-methylbenzoyl]-2,3,5,6,7,8-hexahydro-1'-methylspiro[furo[2,3-g]quinoline-3,4'-piperidine], 1'-Methyl-5-[4-(2-methyl-6-(2-oxopyrrolidin-1-yl)pyridin-3-yl)benzoyl]-2,3,6,7-tetrahydrospiro[furo[2,3-f]indole-3,4'-piperidine], 5-[4-(2-Methyl-6-(2-oxopyrrolidin-1-yl)pyridin-3-yl)benzoyl]-2,3,6,7-tetrahydrospiro[furo[2,3-f]indole-3,4'-piperidine], 1'-Methyl-5-[6-(2-methyl-4-(5-methyl-1,3,4-oxadiazol-2-yl)phenyl)nicotinoyl]-2,3,6,7-tetrahydrospiro[furo[2,3-f]indole-3,4'-piperidine], or pharmaceutically acceptable salts or N-oxides thereof.

7. A process for the preparation of a compound of formula (I) which comprises:

(a) for compounds of formula (I) where D is nitrogen and B is oxygen, reaction of a compound of formula (II):

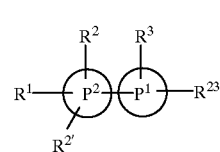

(II)

in which $P^1$, $P^2$, $R^1$, $R^2$ $R^{2'}$ and $R^3$ are as defined in formula (I);

with a compound of formula (III):

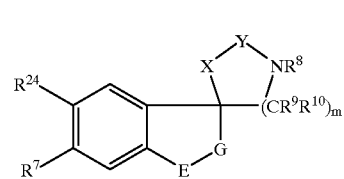

(III)

wherein $R^6$, $R^7$, $R^8$, $R^9$, $R^{10}$, E, G, X, Y, and m are as defined in formula (I) and $R^{23}$ and $R^{24}$ are functional groups which react together to form the A group;

and optionally thereafter in any order:
converting a compound of formula (I) into another compound of formula (I)
forming a pharmaceutically acceptable salt.

8. A pharmaceutical composition which comprises a 5HT1B receptor antagonistic effective amount of a compound according to claim 1 in association with a pharmaceutically acceptable carrier or excipient.

* * * * *